United States Patent [19]

Pedain

[11] Patent Number: 5,144,031
[45] Date of Patent: Sep. 1, 1992

[54] PROCESS FOR THE PRODUCTION OF ISOCYANURATE POLYISOCYANATES, THE COMPOUNDS OBTAINED BY THIS PROCESS AND THEIR USE

[75] Inventor: Josef Pedain, Cologne, Fed. Rep. of Germany

[73] Assignee: Bayer Aktiengesellschaft, Leverkusen, Fed. Rep. of Germany

[21] Appl. No.: 696,433

[22] Filed: May 6, 1991

[30] Foreign Application Priority Data

May 11, 1990 [DE] Fed. Rep. of Germany ....... 4015155

[51] Int. Cl.$^5$ .................... C07D 251/34; C08G 18/79
[52] U.S. Cl. .................... 544/193; 252/182.2; 252/182.21; 252/182.22; 528/45; 528/59; 528/76; 528/80; 528/85; 528/49; 544/222; 560/330
[58] Field of Search .......... 252/182.2, 182.21, 182.22; 528/45, 59, 76, 80, 85, 49; 544/193, 222; 560/330

[56] References Cited

U.S. PATENT DOCUMENTS

| | | | |
|---|---|---|---|
| 3,487,080 | 12/1969 | Matsui et al. | 544/193 |
| 3,635,848 | 1/1972 | Rambosek | 252/182.22 |
| 3,891,579 | 6/1975 | Cenker et al. | 528/49 |
| 4,128,537 | 12/1978 | Markiewitz | 528/51 |
| 4,145,544 | 3/1979 | Kuehn | 544/193 |
| 4,159,376 | 6/1979 | Kuehn | 544/222 |
| 4,302,351 | 11/1981 | Gras et al. | 252/182.21 |
| 4,324,879 | 4/1982 | Bock et al. | 528/45 |
| 4,326,043 | 4/1982 | Narayan et al. | 544/193 |
| 4,359,541 | 11/1982 | Patton, Jr. et al. | 544/193 |
| 4,412,073 | 10/1983 | Robin | 544/193 |
| 4,485,226 | 11/1984 | Noll et al. | 528/45 |
| 4,487,928 | 12/1984 | Richter et al. | 544/193 |
| 4,537,961 | 8/1985 | Robin | 544/193 |
| 4,604,418 | 8/1986 | Shindo et al. | 524/296 |
| 4,675,401 | 6/1987 | Robin | 544/193 |
| 4,789,705 | 12/1988 | Kase et al. | 524/590 |
| 4,870,152 | 9/1989 | Meixner et al. | 528/49 |
| 5,043,092 | 8/1991 | Pedain et al. | 252/182.21 |
| 5,064,960 | 11/1991 | Pedain et al. | 544/222 |
| 5,076,958 | 12/1991 | Pedain et al. | 252/182.2 |

FOREIGN PATENT DOCUMENTS

| | | |
|---|---|---|
| 3240613 | 5/1984 | Fed. Rep. of Germany . |
| 3811350 | 10/1989 | Fed. Rep. of Germany . |
| 61-151179 | 7/1986 | Japan . |
| 920080 | 3/1963 | United Kingdom . |

Primary Examiner—John Kight, III
Assistant Examiner—Rabon Sergent
Attorney, Agent, or Firm—Joseph C. Gil; Thomas W. Roy

[57] ABSTRACT

The present invention relates to a process for the production of isocyanurate group-containing polyisocyanates by partially trimerizing the isocyanate groups of (cyclo)aliphatic diisocyanates in the presence of catalysts which accelerate the trimerization of isocyanate groups and optionally in the presence of an inert solvent, terminating the trimerization reaction at the desired degree of trimerization and removing unreacted starting diisocyanate and any other volatile constituents, characterized in that at least one monohydric alcohol containing ester groups corresponding to the formula $$R-O+CO-(CH_2)_n-O\}_m H$$

is added to the reaction mixture prior to removing the excess starting diisocyanate in a quantity of 1 to 30% by weight, based on the weight of the diisocyanate starting material, and reacted with a portion of the isocyanate groups to form urethane groups, provided that after the trimerization and urethanization reactions, the reaction mixture contains at least 10% by weigth of unreacted starting diisocyanate, based on the weight of the reaction mixture excluding the weight of inert solvent.

The present invention also relates to the isocyanurate polyisocyanates obtained by this process and to their use, optionally after blocking with blocking agents for isocyanate groups, for the production of polyurethane plastics and, more particularly, two-component polyurethane coating compositions.

9 Claims, No Drawings

PROCESS FOR THE PRODUCTION OF ISOCYANURATE POLYISOCYANATES, THE COMPOUNDS OBTAINED BY THIS PROCESS AND THEIR USE

BACKGROUND OF THE INVENTION

1. Field of the Invention

This invention relates to a new process for the production of isocyanurate polyisocyanates containing urethane and ester groups (isocyanurate polyisocyanates) to the compounds obtained by this process and to their use as the polyisocyanate component in the production of polyurethane plastics and more particularly in two-component polyurethane coating compositions.

2. Description of the Prior Art

Aliphatic isocyanurate polyisocyanates, particularly those based on hexane-1,6-diisocyanate (hereinafter referred to as "HDI") have acquired industrial significance. They are used primarily as the polyisocyanate component in two-component polyurethane coating compositions and also for the production of moisture-curing one-component polyurethane binders or, after blocking with blocking agents for isocyanate groups, in heat-crosslinkable polyurethane coating compositions. These coating compositions are mainly used for painting inflexible substrates, such as metals and wood, and are distinguished by their excellent light stability, weathering resistance, hardness and adhesion. HDI-based isocyanurate polyisocyanates may be distinguished from corresponding biuret types, which are also industrially used, by greatly improved resistance to yellowing and chemicals, for example, resistance to tar stains.

The chemical bases of the various polyurethane coating compositions are described inter alia in "Lackkunstharze" by Hans Wagner and Hans Friedrich Sarx, Carl Hanser Verlag, Munchen 1971, pages 153 to 173 and in "Lehrbuch der Lacke und Beschichtungen", Vol. I, Part 2, by Hans Knittel, Verlag W. A. Colomb, Berling-Oberschwandorf 1973, pages 512 to 612.

The production of isocyanurate polyisocyanates is described, for example, in GB-PS 920,080, DE-AS 1,667,309, DE-OS 3,100,262, DE-OS 3,219,608, DE-OS 3,240,613, DE-OS 3,811,350, EP-A 10,589, EP-A 57,653, EP-A 89,297, EP-A 187,105 and Japanese patent application Sho 59-271970 of Dec. 25, 1984 published as Sho 61-151179 on Jul. 9, 1986. The use of substoichiometric quantities of hydroxyl compounds is also mentioned in some of these prior publications. For example, DE-AS 1,667,309 describes the production of isocyanurate polyisocyanates using hydroxyl compounds as co-catalysts. DE-OS 3,219,608 describes the use of polyhydric alcohols having a molecular weight below 3,000 in a quantity of up to 15 mole-%, based on HDI, in the production of isocyanurate polyisocyanates based on HDI. The polyhydric alcohols which are said to be suitable in this prior publication also include polyester polyols which are not specified in detail. Low molecular weight diols bearing lateral alkyl groups are used as modifiers in the process according to EP-A-155,559. The above Japanese publication recommends the use of alkanols having from 6 to 9 carbon atoms as cocatalyst for the trimerization reaction.

The modification of the starting diisocyanate with certain diols containing ester groups in accordance with DE-OS 3,811,350 is intended in particular to increase the elasticity of coatings produced from the modified polyisocyanates, a certain improvement in the compatibility of the modified polyisocyanates also being obtained.

However, one feature common to all known processes for the production of isocyanurate polyisocyanates based on aliphatic diisocyanates, particularly HDI, is that the end products do not entirely satisfy practical requirements in regard to low viscosity and compatibility with hydroxyl-containing paint resins and physiologically substantially safe solvents. In addition, the production of particularly low viscosity isocyanurate polyisocyanates based on HDI has previously only been possible at particularly low conversions of about 10 to 20% of the HDI used. Processes in which the trimerization reaction has to be terminated at a very low degree of trimerization and in which the excess HDI has to be removed by distillation are naturally complicated and expensive.

Accordingly, an object of the present invention is to provide new isocyanurate polyisocyanates based on aliphatic diisocyanates which have both a low viscosity and improved compatibility with known hydroxyl-containing paint resins and known physiologically safe solvents. It is an additionally of the present invention to provide new isocyanurate polyisocyanates which may be produced in an economically advantageous manner at a high conversion of the diisocyanate used.

These objects may be achieved by the process according to the present invention which is described in detail hereinafter.

SUMMARY OF THE INVENTION

The present invention relates to a process for the production of isocyanurate group-containing polyisocyanates by partially trimerizing the isocyanate groups of (cyclo)aliphatic diisocyanates in the presence of catalysts which accelerate the trimerization of isocyanate groups and optionally in the presence of an inert solvent, terminating the trimerization reaction at the desired degree of trimerization and removing unreacted starting diisocyanate and any other volatile constituents, characterized in that at least one monohydric alcohol containing ester groups corresponding to the formula

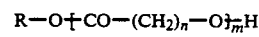

$$R-O+CO-(CH_2)_n-O\}_m H$$

wherein
R is an optionally olefinically unsaturated (cyclo)aliphatic $C_{1-18}$ hydrocarbon radical which may contain ether groups,
m is a whole number or, on a statistical average, a fractional number of 1 to 2 and
n is an integer of 3 to 5, is added to the reaction mixture prior to removing the excess starting diisocyanate in a quantity of 1 to 30% by weight, based on the weight of the diisocyanate starting material, and reacted with a portion of the isocyanate groups to form urethane groups, provided that after the trimerization and urethanization reactions, the reaction mixture contains at least 10% by weight of unreacted starting diisocyanate, based on the weight of the reaction mixture excluding the weight of inert solvent.

The present invention also relates to the isocyanurate polyisocyanates obtained by this process and to their use, optionally after blocking with blocking agents for isocyanate groups, for the production of polyurethane plastics and, more particularly, two-component polyurethane coating compositions.

DETAILED DESCRIPTION OF THE INVENTION

Starting materials for the process according to the invention include (i) (cyclo)aliphatic diisocyanates and (ii) selected monohydric polyester alcohols.

The (cyclo)aliphatic diisocyanates used as starting diisocyanate (i) are organic diisocyanates containing aliphatically and/or cycloaliphatically bound isocyanate groups. Examples include hexane-1,6-diisocyanate (HDI), 3,3,5-trimethyl-5-isocyanatomethyl cyclohexane-1-isocyanate (IPDI) and dicyclohexyl methane-4,4'-diisocyanate. When (cyclo)aliphatic diisocyanates other than HDI are used, it is preferred to use them in admixture with HDI. This means that the preferred starting diisocyanates to be used in accordance with the invention are either HDI or mixtures of HDI with other (cyclo)aliphatic diisocyanates, preferably those of the type set forth above, provided that the mixtures contain at least 30 mole-%, preferably at least 70 mole-% of HDI. In a particularly preferred embodiment, HDI is used as sole starting diisocyanate.

The diisocyanates used as starting materials in accordance with the invention may be used in the purity obtained in commercially available form. However, in a particularly preferred embodiment, HDI substantially freed from carbon dioxide is used as sole starting diisocyanate because its use provides for a particularly mild trimerization reaction using minimal quantities of catalysts.

The HDI used with particular preference as the starting diisocyanate has a carbon dioxide content of less than 20 ppm, preferably less than 10 ppm and more preferably less than 5 ppm.

Commercially available HDI, which has been purified by distillation after its preparation and which has previously been used for the production of isocyanurate polyisocyanates, contains considerable quantities (approx. 20 ppm to 100 ppm) of carbon dioxide.

Carbon dioxide can enter HDI during the production process, for example, during the phosgenation of carbonic acid salts of hexamethylene diamine. It can be absorbed from the air during storage and can be formed by chemical reaction of the NCO groups, for example, by carbodiimide formation or by reaction with moisture. HDI freshly purified by vacuum distillation contains 40 ppm of carbon dioxide after 24 hours in a sealed container. HDI stored over a period of about 6 months can contain up to 0.6% by weight carbon dioxide if the container has been opened during storage.

Carbon dioxide can be removed by bubbling or passing high purity nitrogen or a noble gas such as argon through the HDI, for example, at 0° to 70° C. Although a higher temperature may be applied, this does not afford any significant advantage.

It is also possible and preferred to initially modify HDI containing more than 20 ppm carbon dioxide with a substoichiometric quantity of ester alcohol in accordance with the invention, prior to removing the dissolved carbon dioxide and carrying out the trimerization reaction.

The monohydric ester alcohols (ii) are compounds corresponding to the formula

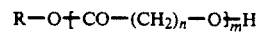

wherein
R, m and n are as already defined.
Preferred ester alcohols are those corresponding to the formula wherein
R is a saturated aliphatic $C_{1-12}$ hydrocarbon radical,
m is a whole or fractional number of 1 to 2 and
n is 5.

The molecular weight of these monohydric ester alcohols is about 146 to 412, preferably about from 160 to 300.

The monohydric ester alcohols are prepared by reacting the corresponding alcohols R-OH, which are free from ester groups, with lactones such as butyrolactone, valerolactone and, in particular, caprolactone. This known reaction may be carried out, for example, in the presence of catalysts, e.g., boron trifluoride etherate or organotin compounds such as tin dioctoate at temperatures of 120° to 200° C.

The monohydric ester alcohols (ii) are generally mixtures because the addition of the lactones onto the alcohols does not lead to uniform products but instead, in accordance with the foregoing observations with regard to m, to mixtures in which individual compounds having different values for m are present. In addition, mixtures can be present simply because mixtures of different alcohols free from ester groups and/or mixtures of different lactones can be used in the production of the ester alcohols. Since m is a statistical mean value, certain contents of alcohols R-OH free from ester groups can still be present in the mixtures, even if m on a statistical average is 1 or greater than 1.

The process according to the invention may be carried out analogously to the known processes for the production of isocyanurate polyisocyanates. This means in particular that the known trimerization catalysts, as disclosed for example in the literature references cited above, may be used.

Quaternary ammonium hydroxides are preferably used as catalyst in the process according to the invention. Any quaternary ammonium hydroxides of the type already recommended as trimerization catalysts for isocyanate groups are basically suitable. For example, the quaternary ammonium hydroxides disclosed in U.S. Pat. Nos. 3,487,080 and 4,324,879, both of which are herein incorporated by reference, are suitable catalysts. Compounds corresponding to the formula

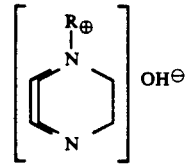

wherein
R is an alkyl group containing 1 to 20, preferably 1 to 4 carbon atoms; an araliphatic hydrocarbon radical containing 7 to 10, preferably 7 carbon atoms; or a saturated cycloaliphatic hydrocarbon radical containing 4 to 10, preferably 5 to 6 carbon atoms,
are also suitable catalysts.

Preferred catalysts are compounds corresponding to the formula

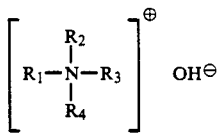

in which
R₁, R₂ and R₃ may be the same or different and represent alkyl groups containing 1 to 18, preferably 1 to 4 carbon atoms and more preferably methyl groups, and R₄ is a benzyl, 2-hydroxyethyl, 2-hydroxypropyl or 2-hydroxybutyl group.

Particularly preferred catalysts are N,N,N-trimethyl-N-benzyl-ammonium hydroxide and N,N,N-trimethyl-N-(2-hydroxypropyl)-ammonium hydroxide.

The optimum quantity of catalyst depends upon the type of catalyst and may be determined in a corresponding preliminary test. In the process according to the invention, the quantity in which the catalyst is used is generally below 1% by weight, based on the starting diisocyanate used. When HDI, which has largely been freed from carbon dioxide in accordance with the foregoing observations, is used as the starting diisocyanate and when the preferred ammonium hydroxide catalysts are used, the quantity of catalyst required is less than 0.03% by weight, preferably less than 0.01% by weight and, more preferably, from 0.0005 to 0.005% by weight, based on the weight of HDI.

The catalysts may be used in solventless form, although they are preferably used in the form of dilute solutions. Suitable solvents are described in the cited publications.

Trimerization and urethanization reactions are preferably carried out in the absence of solvents, although this does not preclude the use of known paint solvents, e.g., esters such as butyl acetate or ethoxyethyl acetate; ketones such as methyl isobutyl ketone or methyl ethyl ketone; hydrocarbons such as xylene; and mixtures of such solvents. However, since unreacted starting diisocyanate is subsequently removed, the presence of such solvents would involve unnecessary additional effort.

To terminate the trimerization reaction, the catalyst is either thermally deactivated and/or a suitable catalyst poison is added to the reaction mixture to deactivate the catalyst. Suitable catalyst poisons, particularly when the preferred ammonium hydroxide catalysts are used, include inorganic acids such as hydrochloric acid, phosphorous acid or phosphoric acid; sulfonic acids or derivatives thereof such as methane sulfonic acid, p-toluene sulfonic acid, or p-toluene sulfonic acid methyl or ethyl ester; and perfluorinated sulfonic acids such as nonafluorobutane sulfonic acid. Particularly suitable deactivators, i.e., catalyst poisons, are acidic esters of phosphorous acid or phosphoric acid, such as dibutyl phosphite, dibutyl phosphate or di-(2-ethylhexyl)-phosphate, which are preferably used in the form of a dilute solution in HDI. The deactivators are generally added to the reaction mixture in at least an equivalent quantity to the catalyst. However, since the catalysts can partly decompose during the trimerization reaction, it is often sufficient to add a subequivalent quantity of the deactivator. When thermally labile catalysts are used, for example, quaternary ammonium hydroxides which are hydroxyalkyl-substituted at the nitrogen, there is often no need to add a catalyst poison at all because the reaction may often be terminated simply by briefly heating the reaction mixture to temperatures above 100° C. to thermally decompose the catalyst. In order to guarantee safe termination of the reaction, it is often preferred to use more than the equivalent quantity, for example twice the equivalent quantity, of deactivator. Accordingly, it is preferred to use deactivators (catalyst poisons) in up to twice the equivalent quantity, based on the quantity of catalyst used.

A critical feature of the present invention is that, in addition to partial trimerization of the isocyanate groups of the starting diisocyanate, some of the isocyanate groups are modified by urethanization with the ester alcohols previously set forth. The order in which urethanization and trimerization take place is not important, provided that both process steps are carried out before removal of the excess starting diisocyanate. This means that the urethanization reaction with the ester alcohol in which the isocyanate groups are partly consumed may take place before addition of the trimerization catalyst. The urethanization reaction may also be carried out with only part of the excess diisocyanate and more diisocyanate may be added before the subsequent trimerization reaction. The urethanization and trimerization reactions may be carried out at the same time by simultaneously adding ester alcohol and trimerization catalyst, for example in admixture. The urethanization reaction may be started before the trimerization reaction is terminated; it may also be started after the trimerization reaction.

The ester alcohol may also be added in portions at any time during the process. The trimerization and urethanization reactions should be terminated before the removal of excess starting diisocyanate is commenced.

The ester alcohols are generally used in a quantity of 1 to 30% by weight, preferably 5 to 20% by weight, based on the weight of the diisocyanate starting material. Measures are preferably taken to ensure that the starting diisocyanate is always used in an excess such that, on completion of the reactions, the reaction mixture still contains at least 10% by weight, preferably 35 to 70% by weight, based on the mixture as a whole excluding any inert solvents, of unreacted starting diisocyanate. The molar ratio of isocyanurate groups to urethane groups in the end products freed from excess starting diisocyanate should preferably be 40:1 to 5:1.

The process according to the invention is generally carried out at a temperature of 0° to 150° C. The urethanization reaction, which may be carried out separately before or after the trimerization reaction, preferably takes place at 20° to 150° C., more preferably at 80° to 130° C. The trimerization reaction, which may be carried out separately before or after the urethanization reaction preferably takes place at a temperature of 0° to 100° C., more preferably at 20° to 80° C. If both reaction steps are carried out at the same time, the reaction temperature is preferably 0° to 100° C., more preferably 40° to 80° C.

The trimerization reaction is terminated thermally and/or by the addition of a catalyst poison, preferably after a degree of trimerization of 10 to 40%, more preferably 20 to 30% has been achieved. The "degree of trimerization" is the percentage of isocyanate groups of the starting diisocyanate which react during the trimerization reaction; the urethanization reaction is not included in this calculation. As mentioned above, however, it is essential that at least 10% by weight unreacted starting diisocyanate be present in the reaction mixture after the urethanization and trimerization reactions are complete.

After urethanization and trimerization, the excess starting diisocyanate is removed by suitable means to the residual starting diisocyanate content is at most 0.5% by weight. Optionally other volatile constituents present in the reaction mixture, such as any solvent used, may also be removed. This may be done by thin-layer distillation or by extraction, for example, using n-hexane as the extractant.

The products containing urethane and isocyanurate groups obtained by the process according to the invention are liquid, substantially colorless polyisocyanates. The HDI-based products obtained by the process according to the invention have an NCO content of 10 to 20% by weight. Their color value on the HAZEN scale (DIN 53 409) is below 100, preferably below 50. Their viscosity at 23° C. is below 5,000, preferably below 1,500 mPa.s. Based on a comparable conversion of the isocyanate groups of the starting diisocyanate as a basis, the viscosity of the products obtained by the process according to the invention is considerably less than the viscosity of corresponding isocyanurate polyisocyanates produced without using the ester alcohols essential to the invention.

The products obtained by the process according to the invention are soluble in typical solvents, such as esters, ketones and hydrocarbons, and can be diluted therewith without the formation of cloudiness and are distinguished by high stability in storage. They are substantially free from secondary products. They are eminently suitable as hardeners for two-component polyurethane coating compositions containing typical polyether polyols, polyester polyols and/or polyacrylate polyols as polyhydroxyl reactants for the polyisocyanates. Particularly preferred reactants for the products obtained by the process according to the invention are hydroxyl-containing polyacrylates, i.e., polymers and copolymers of alkyl (meth)acrylates, optionally with styrene or other copolymerizable olefinically unsaturated monomers.

The auxiliaries and additives typically used in paint technology, such as pigments, flow control agents, catalysts, solvents and the like, may of course be incorporated in the two-component polyurethane coating compositions which contain the previously mentioned polyhydroxyl compounds and the polyisocyanates of the present invention as binders and hardeners. The two-component polyurethane coating compositions harden at room temperature or slightly elevated temperature to form paint films resistant to chemicals.

It is of course also possible to use the products obtained by the process according to the invention as hardeners in heat-crosslinkable, one-component coating compositions after blocking the isocyanate groups with blocking agents. Suitable blocking agents are known and include aromatic alcohols such as phenol, cresols, trimethyl phenols and tert. butyl phenols; tertiary alcohols such as tert. butanol, tert. amyl alcohol and dimethyl phenyl carbinol; compounds which readily form enols such as ethyl acetoacetate, acetyl acetone and malonic acid diethyl ester; secondary aliphatic and aromatic amines such as dibutyl amine, N-methyl aniline, the N-methyl toluidines, N-phenyl toluidine and N-phenyl xylidine; imides such as succinimide; lactams such as ε-caprolactam and δ-valerolactam; oximes such as butanone oxime and cyclohexanone oxime; mercaptans, such as methyl mercaptan, ethyl mercaptan, butyl mercaptan, 2-mercapto-benzthiazole, α-naphthyl mercaptan and dodecyl mercaptan; and triazoles such as 1H-1,2,4-triazole.

The products obtained by the process according to the invention may also be combined with polyamines having amino groups which are are blocked, for example, to form polyketimines, polyaldimines or oxazolidines. Free amino groups and (in the case of the oxazolidines) free OH groups, which are formed in the presence of moisture, react with the NCO groups in a cross-linking reaction.

In the coating compositions mentioned, the polyisocyanate component and the reactant are present in quantities such that for every (optionally blocked) NCO group, there are 0.8 to 3, preferably 0.9 to 1.8 (optionally blocked) isocyanate-reactive groups.

Coating compositions containing the products obtained by the process according to the invention, optionally in blocked form, as hardeners are suitable for coating any substrates. They are distinguished from corresponding coating compositions containing known polyisocyanates as hardeners by increased flexibility of the coatings. Preferred applications for the products obtained by the process according to the invention are as hardeners for two-component polymer coating compositions based on the previously mentioned polyhydroxyl compounds, particularly for the painting of flexible plastic parts.

The coating compositions containing the polyisocyanates according to the invention provide films which adhere surprisingly well to metallic substrates and which show particularly high light stability, heat stability and abrasion resistance. In addition, they are distinguished by excellent hardness, elasticity, resistance to chemicals, gloss, weathering resistance and pigmentability.

In the following examples, all parts and percentages are by weight unless otherwise indicated.

EXAMPLE 1

Preparation of alcohol containing ester groups 114 g (1 mole) caprolactone were added to and mixed with 130 g (1 mole) 2-ethyl hexanol and, after addition of 0.024 g tin dioctoate, the resulting mixture was reacted with stirring for 5 h at 160° C. A liquid, colorless product having a hydroxyl value of 230 was obtained. A gas chromatogram showed that approximately 10% by weight of the starting alcohol had not reacted. Free caprolactone was no longer present. In addition to the main substance (i.e., the ester alcohol of 1 mole 2-ethyl hexanol and 1 mole caprolactone), relatively high molecular weight components were also present.

EXAMPLE 2

Example 2 describes the production in accordance with the invention of a low viscosity isocyanurate polyisocyanate at an average conversion.

1,680 g HDI were heated for 3 h at 100° C. with 24.4 g the ester alcohol set forth in Example 1. A stream of high-purity nitrogen was passed through the reaction mixture during the urethanization reaction to remove carbon dioxide.

After cooling to 45° C., 20 g of a 0.5% solution of benzyl trimethyl ammonium hydroxide in 2-ethyl hexanol were added dropwise as catalyst. The exothermic trimerization reaction began immediately. The temperature was kept at about 55° to 60° C. and a gentle stream of nitrogen was again passed through the reaction mixture. After about 7 h, an NCO content of 40.7% was reached. The reaction was terminated by the addition of 0.3 g of a 25% solution of dibutyl phosphate in HDI. After cooling to 25° C., excess HDI was removed by distillation in a short-path evaporator at 130° C. 570 g of a liquid, clear polyisocyanate having the following properties were obtained:

| viscosity: | 1,140 mPa./23° C. |
|---|---|
| NCO content: | 21.5% |
| Hazen color value: | 20 |
| Free HDI: | 0.01 |

When this example was repeated without the addition of the monoalcohol containing ester groups and by terminating the trimerization reaction at approx. 41% NCO, a product having a viscosity of 3,500 mPa.s/23° C. was obtained.

EXAMPLE 3

This Example describes the production of a particularly low-viscosity isocyanurate polyisocyanate.

Example 2 was repeated by reacting 1,680 g HDI with 61 g of the monoalcohol of Example 1. The mixture was polymerized with 15 g of the catalyst solution and the reaction was terminated by addition of dibutyl phosphate solution at an NCO content of approximately 41%. After removal of excess HDI, 554 g of a polyisocyanate having the following properties were obtained:

| NCO content: | 20.0% |
|---|---|
| viscosity: | 810 MPa.s/23° C. |
| Free HDI: | 0.01% |
| Hazen color value: | 30 |

EXAMPLE 4

This Example describes the production of a relatively low viscosity polyisocyanate according to the invention in a very high yield.

Example 3 was repeated with the exception that the reaction was not terminated until the NCO content in the crude product was 31.7%. After the removal of free HDI, 1,030 g of a product having the following properties were obtained:

| viscosity: | 4,850 mPa.s/23° C. |
|---|---|
| NCO content: | 18.8% |
| Free HDI: | 0.01% |
| Hazen color value: | 30 |

EXAMPLE 5

This Example describes a low viscosity product obtained in a high yield. The procedure was the same as set forth in Example 2. The quantities used were as follows:

1,680 g HDI
122 g monoalcohol of Example 1
25 g of the 0.5% catalyst solution
0.5 g of the 25% solution of dibutyl phosphate in HDI.

After the removal of excess HDI, 1,073 g of a clear liquid polyisocyanate having the following properties were obtained:

| Viscosity: | 3,300 mPa./23° C. |
|---|---|
| NCO content: | 18.2% |
| Free HDI: | 0.01% |
| Hazen color value: | 30 |

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the production of an isocyanurate group-containing polyisocyanate which comprises
   a) partially trimerizing the isocyanate groups of a (cyclo)aliphatic diisocyanate in the presence of a catalyst which accelerates the trimerization of isocyanate groups and optionally in the presence of an inert solvent,
   b) terminating the trimerization reaction at the desired degree of trimerization required and
   c) removing unreacted starting diisocyanate and any other volatile constituents,
   said process additionally comprising
   d) adding to the reaction mixture prior to step c) 1 to 30% by weight, based on the weight of said diisocyanate, of at least one monohydric alcohol containing ester groups and corresponding to the formula

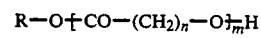

wherein
   R is an optionally olefinically unsaturated (cyclo)aliphatic $C_{1-18}$ hydrocarbon radical which may contain ether groups,
   m is a whole or a fractional number having a value from 1 to 2 and
   n is an integer of 3 to 5,
   and reacting said alcohol with a portion of the isocyanate groups present to form urethane groups, provided that on completion of the reactions of steps a) and d), the reaction mixture contains at least 10% by weight of unreacted diisocyanate, based on the weight of the reaction mixture excluding inert solvent.

2. The process of claim 1 wherein
   R is a saturated aliphatic $C_{1-12}$ hydrocarbon radical and
   n is 5.

3. The process of claim 1 wherein said diisocyanate comprises hexane-1,6-diisocyanate.

4. The process of claim 2 wherein said diisocyanate comprises hexane-1,6-diisocyanate.

5. An isocyanurate group-containing polyisocyanate which is prepared by a process which comprises
   a) partially trimerizing the isocyanate groups of a (cyclo)aliphatic diisocyanate in the presence of a catalyst which accelerates the trimerization of isocyanate groups and optionally in the presence of an inert solvent,
   b) terminating the trimerization reaction at the desired degree of trimerization required and c) removing unreacted starting diisocyanate and any other volatile constituents, said process additionally comprising d) adding to the reaction mixture prior to step c) 1 to 30% by weight, based on the weight of said diisocyanate, of at least one monohydric alcohol containing ester groups and corresponding to the formula $$R-O+CO-(CH_2)_n-O\frac{1}{m}H$$

wherein

R is an optionally olefinically unsaturated (cyclo)aliphatic $C_{1-18}$ hydrocarbon radical which may contain ether groups, m is a whole or a fractional number having a value from 1 to 2 and n is an integer of 3 to 5, and reacting said alcohol with a portion of the isocyanate groups present to form urethane groups, provided that on completion of the reactions of steps a) and d), the reaction mixture contains at least 10% by weight of unreacted diisocyanate, based on the weight of the reaction mixture excluding inert solvent.

6. The polyisocyanate of claim 5 wherein
R is a saturated aliphatic $C_{1-12}$ hydrocarbon radical and
n is 5.

7. The polyisocyanate of claim 5 wherein said diisocyanate comprises hexane-1,6-diisocyanate.

8. The polyisocyanate of claim 6 wherein said diisocyanate comprises hexane-1,6-diisocyanate.

9. A composition comprising the isocyanurate group-containing polyisocyanate of claim 5, wherein the isocyanate are optionally blocked with blocking agents, and a compound which contains at least two isocyanate-reactive groups.

* * * * *